United States Patent [19]

Sauer et al.

[11] Patent Number: 5,105,008
[45] Date of Patent: Apr. 14, 1992

[54] PROCESS FOR PREPARING SOLID BETAINES

[75] Inventors: Joe D. Sauer; Kim R. Smith; James E. Borland; Jeffrey W. Perine, all of Baton Rouge, La.

[73] Assignee: Ethyl Corporation, Richmond, Va.

[21] Appl. No.: 723,919

[22] Filed: Jul. 1, 1991

[51] Int. Cl.$^5$ .......................................... C07C 229/00
[52] U.S. Cl. ...................... 562/575; 560/156; 560/170; 562/443; 562/444; 562/553; 562/567
[58] Field of Search .............. 562/575, 567, 553, 443, 562/444; 560/156, 170

[56] References Cited

U.S. PATENT DOCUMENTS

| | | | |
|---|---|---|---|
| 2,082,275 | 6/1937 | Daimler | 562/575 |
| 2,129,264 | 9/1938 | Downing | 562/575 |
| 2,564,507 | 8/1951 | Schaeffer | 562/575 |
| 2,800,502 | 7/1957 | Vassel | 562/575 |
| 3,480,665 | 11/1969 | Nagy | 562/575 |
| 3,555,079 | 1/1971 | Murumo | 260/501.13 |
| 3,649,677 | 3/1972 | Morris | 562/567 |
| 3,954,845 | 5/1976 | Martinsson | 562/567 |
| 4,832,871 | 5/1989 | Bade | 252/546 |

FOREIGN PATENT DOCUMENTS 1185111  3/1970  United Kingdom.

OTHER PUBLICATIONS

Nandakumar, "Journal of the Oil Technologists' Association of India," vol. 11(2), pp. 31-34 (1979).

Primary Examiner—Michael L. Shippen
Attorney, Agent, or Firm—Patricia J. Hogan

[57] ABSTRACT

Betaines are produced in solid form by reacting a tert-amine with an alkyl haloalkanoate and hydrolyzing the resultant quaternary ammonium ester when the tert-amine/alkyl haloalkanoate reaction is conducted in a liquefied gas as the solvent and the hydrolysis is conducted in a liquefied gas solvent or a polar aprotic solvent in which the betaine is substantially insoluble. In a preferred embodiment, the tert-amine is an N-alkyl-dimethylamine, the haloalkanoate is ethyl chloroacetate, and the liquefied gas is carbon dioxide.

16 Claims, No Drawings

PROCESS FOR PREPARING SOLID BETAINES

FIELD OF THE INVENTION

This invention relates to a process for preparing solid betaines from quaternary ammonium esters.

BACKGROUND

As disclosed in British Patent 1,185,111 (Morris) and U.S. Pat. Nos. 2,082,275 (Daimler et al.), 3,555,079 (Marumo et al.), and 4,832,871 (Bade), it is known that tert-amines can be quaternized with haloalkanoate salts in water or a polar aprotic solvent to prepare betaines in solution form, most commonly as 30–35% active aqueous solutions.

Nandakumar et al., *Journal of the Oil Technologists' Association of India*, Volume 11(2), pp. 31–35 (1979) show that it is also known that a betaine solution can be obtained by reacting the tert-amine with a haloalkanoate ester to form a quaternary ammonium ester and then reacting the intermediate with a base to convert it to the corresponding betaine.

Solid betaines have the advantages over betaine solutions that they can be transported at lower costs and offer more flexibility in the formulation of products from betaines. It is possible to recover solid betaines from the solutions described above, but it would be preferable to be able to prepare the betaines directly in solid form.

Copending application Ser. No. 07/652,616 (Borland et al.), now U.S. Pat. No. 5,081,293, discloses a process whereby betaines are prepared in solid form by conducting the tert-amine/alkyl haloalkanoate and subsequent quaternary ammonium ester/base reactions in polar aprotic solvents in which the betaines are substantially insoluble.

SUMMARY OF THE INVENTION

It has now been found that solid betaines can be produced by reacting a tert-amine with an alkyl haloalkanoate in a liquefied gas solvent to form a quaternary ammonium ester and then hydrolyzing that intermediate in a liquefied gas solvent or in a polar aprotic solvent in which the betaine is substantially insoluble.

DETAILED DESCRIPTION

As evidenced by the variety of types of tert-amines which have been quaternized with haloalkanoates in the past, the particular tert-amine used in the process is not critical. It may be, e.g., any of the tert-amines of Morris, Daimler et al., Marumo et al., and Bade, the teachings of all of which are incorporated herein by reference.

The tert-amines which are generally most valuable to employ in the reaction are those in which at least one of the N-substituents is an alkyl or hydroxyalkyl group and the remaining N-substituents are aliphatic or cyclic organic groups which may be hydrocarbyl or non-hydrocarbyl in nature, e.g., alkyl, hydroxyalkyl, polyoxyethylene, alkylamidoalkyl, phenyl, or benzyl, including those in which an alkyl or hydroxyalkyl group is attached to a nitrogen which is a member of a heterocyclic ring, such as a morpholine ring.

Among the preferred tert-amines are the compounds corresponding to the formula RR'R"N in which R is a linear or branched-chain alkyl group containing 6–22 carbons, more preferably a primary alkyl group containing 8–18 carbons; R' is methyl, ethyl, or 2-hydroxyethyl; and R" is independently selected from methyl, ethyl, 2-hydroxyethyl, and linear and branched-chain alkyl groups containing 6–22 carbons. These tert-amines may be used alone or in combination to provide, e.g.:

(1) a single RR'R"N amine in which R is either a linear or a branched-chain alkyl group containing a given number of carbons, (2) a mixture of RR'R"N amines in which the R of one component of the mixture is a linear alkyl group containing a given number of carbons and the R of another component of the mixture is a branched-chain alkyl group containing the same number of carbons, (3) a mixture of RR'R"N amines in which the R of one component of the mixture is a linear alkyl group containing a given number of carbons and the R of another component of the mixture is a linear alkyl group containing a different number of carbons, or (4) a mixture of RR'R"N amines in which the R of one component of the mixture is a linear alkyl group containing a given number of carbons, the R of another component is a branched-chain alkyl group containing the same number of carbons, and the R of another component of the mixture is a linear or branched-chain alkyl group containing a different number of carbons.

The most preferred of these tert-amines are those in which at least a majority of alkyl groups in the tert-amine or tert-amine mixture are linear and R' and R" are independently selected from methyl, ethyl, and 2-hydroxyethyl, especially those in which both R' and R" are methyl.

The haloalkanoate which is reacted with the tert-amine to form the quaternary ammonium ester is an alkyl ester of an ω-haloalkanoic acid in which the halo substituent is chloro, bromo, or iodo. These haloalkanoates are compounds wherein neither the size nor the degree of linearity of the alkyl or alkanoic moiety is critical, and they thus include compounds in which both moieties are large or small or in which one is small and the other large and in which both moieties are linear or branched or in which one is linear and the other branched. However, most commonly both the alkyl and the alkanoic moieties are moieties containing up to about 30 carbons; and it is preferred that any branching in the alkanoic moiety be confined to carbons other than the carbon to which the halo substituent is attached, since any branching on that carbon could be expected to slow the reaction significantly.

Exemplary of the alkyl haloalkanoates that can be used are the methyl, ethyl, propyl, isopropyl, butyl, isobutyl, pentyl, hexyl, octyl, 2-ethylhexyl, decyl, dodecyl, eicosyl, and triacontyl esters of chloroacetic, chloropropionic, chlorobutyric, chloropentanoic, chlorohexanoic, chloroheptanoic, chloro-β-ethylhexanoic, and corresponding bromo- and iodoalkanoic acids. The preferred haloalkanoates are compounds corresponding to the formula $X(CH_2)_nCOOZ$ in which X is chloro, bromo, or iodo, Z is a linear or branched-chain alkyl group containing 1–6 carbons; and n is an integer of 1–6. Ordinarily, the most preferred alkyl haloalkanoates are the methyl and ethyl chloroacetates.

The amount of haloalkanoate employed to quaternize the tert-amine is usually at least the stoichiometric amount. However, it is preferred not to use too much of the haloalkanoate reactant, so it can be most preferable to utilize the reactants in substantially stoichiometric amounts.

The liquefied gas used as the reaction medium in the quaternization step of the process may be the liquefied form of any normally gaseous material which is inert in the sense that it will neither prevent the reaction from occurring nor react with the product. Such normally gaseous materials include, e.g., air, oxygen, carbon dioxide, nitrogen, argon, ethylene, methane, ethane, propane, butane, isobutane, trifluoromethane, tetrafluoromethane, chlorotrifluoromethane, and mixtures thereof.

Most commonly, the liquefied gas which is employed is one that is commercially available and ca simply be introduced into the reaction vessel in liquid form and maintained in liquid form by the use of pressure. However, if desired, it may be acquired in the gaseous state and introduced into the reaction vessel via a compressor to liquefy it.

Because of the greater expense involved in liquefying a gas which has a very low critical temperature, it is frequently preferred to employ as the liquefied gas a normally gaseous material which has a critical temperature that is above or not much below room temperature, generally a critical temperature of at least 0.C, preferably at least 20.C, e.g., materials such as ethylene, carbon dioxide, chlorotrifluoromethane, ethane, propane, butane, and isobutane.

The quaternization step of the process of the invention is conducted by combining the tert-amine with the alkyl haloalkanoate in the liquefied gas solvent and allowing the quaternization reaction to occur. Although the reaction can be effected at room temperature, it is ordinarily preferred to use an elevated temperature, preferably a temperature in the range of about 50-150° C., to speed the reaction. The process is conducted under a pressure sufficient to maintain the liquefied gas in the liquid state, most commonly a pressure consistent with conducting an economical process, usually a pressure in the range of about 4.9-8.5 MPa.

In general, the reaction may be conducted so as to have supercritical or subcritical conditions.

After completion of the quaternization reaction, the system is vented to remove the liquefied gas when it is desired to hydrolyze the quaternary ammonium ester in an organic solvent, or a base is added to the system when it is desired to conduct both steps of the process in the liquefied gas solvent.

Regardless of whether the hydrolysis is conducted in a liquefied gas or in an organic solvent, the base employed to convert the quaternary ammonium ester to the betaine may be any of the bases conventionally used in such reactions, usually aluminum hydroxide or the hydroxide of a Group IA or IIA metal, such as lithium, sodium, potassium, rubidium, cesium, beryllium, magnesium, calcium, strontium, or barium. It is ordinarily used in the stoichiometric amount to effect complete reaction, and the preferred base is generally sodium hydroxide.

Although the base may be utilized in virtually any form, e.g., as a powder, pellets, or aqueous or alcoholic solution, the more dilute solutions, i.e., those containing less than about 25% of the base, are not very desirable for use in the process because of the objective of preparing the betaine in solid form. The large amount of water contributed by a dilute aqueous solution of the base could solubilize the betaine and/or cause foaming if later concentration of the product were to become necessary.

The hydrolysis is accomplished by contacting the base with the quaternary ammonium ester in the presence of the liquefied gas or polar aprotic solvent and allowing the base to react with the ester and remove the esterifying group. The hydrolysis, like the quaternization, can be effected at room temperature but is preferably conducted at a higher temperature, e.g., about 50-150° C.

When the solvent is a polar aprotic solvent, the reaction may be accomplished at atmospheric or subatmospheric pressure but is preferably conducted under superatmospheric pressure, e.g., a pressure of about 0.1-2.1 MPa. When the solvent is a liquefied gas, the reaction is conducted under a pressure sufficient to maintain the liquefied gas in the liquid state, preferably a pressure of about 4.9-8.5 MPa.

Processes in which a liquefied gas is used as the solvent for both the quaternization and the hydrolysis steps have a certain economic advantage. However:

(1) they can limit the choices as to liquefied gases which may be used, since a liquefied gas which would be inert to the quaternization reaction would not necessarily permit the hydrolysis to occur, and (2) the use of a liquefied gas rather than an organic solvent for the hydrolysis reaction leaves the betaine product contaminated with salt and alcohol by-products which might have to be removed by solvent extraction or evaporation, e.g., when the byproducts would detrimentally affect the properties of the betaine in a particular application and/or when an alcohol by-product would solubilize a substantial amount of the product.

Thus, it is often preferable to conduct the hydrolysis step in a polar aprotic solvent in which the betaine is substantially insoluble.

It is critical that any polar aprotic solvent used for the hydrolysis reaction be a solvent in which the betaine is substantially insoluble, at least at room temperature, to accomplish the objective of preparing a betaine which is easily recovered in solid form. Suitable solvents include, e.g., ketones such as 2-propanone, 2-butanone, 3-methyl-2-butanone, 2-pentanone, and 3-pentanone; cyclic ethers such as tetrahydrofuran, tetrahydropyran, and dioxane; and sulfoxides such as dimethylsulfoxide. When such solvents are used, the preferred solvents are the ketones, especially 2-butanone.

Because of the insolubility of the betaine product in the polar aprotic solvent, it is easily recovered as a solid by filtration when such a solvent is used in the hydrolysis reaction; and the product is easily recovered by venting the system when a liquefied gas is used as the solvent in the reaction. In either case, the solid thus recovered is a betaine having high activity; and its activity can be increased to an even higher level, in fact to as high as 100%, by removing some-to-all of the salt by-product of the base reaction and any remaining solvent, if desired.

The invention is advantageous as a convenient means of preparing solid betaines which can be used in the same applications as conventional betaine solutions, e.g., in the production of soaps and shampoos, but which offer more flexibility in the formulation of products because of not having any solvent associated therewith and which are also more economical to transport.

What is claimed is:

1. In a process for preparing a betaine by reacting a tert-amine with an alkyl haloalkanoate to form a quaternary ammonium ester and then hydrolyzing that ester in the absence of a solvent in which the betaine would be soluble at room temperature, the improvement which comprises conducting the tert-amine/alkyl haloalkanoate reaction in a liquefied gas as the solvent.

2. The process of claim 1 wherein the tert-amine is a compound corresponding to the formula RR'R"N in which R is an alkyl group containing 6-22 carbons; R' is methyl, ethyl, or 2-hydroxyethyl; and R" is independently selected from methyl, ethyl, 2-hydroxyethyl, and alkyl groups containing 6-22 carbons.

3. The process of claim 2 wherein R is a primary alkyl group containing 8-18 carbons and R' and R" are independently selected from methyl, ethyl, and 2-hydroxyethyl.

4. The process of claim 3 wherein R' and R" are methyl.

5. The process of claim 2 wherein R and R" are independently selected from primary alkyl groups containing 8-18 carbons.

6. The process of claim 5 wherein R' is methyl.

7. The process of claim 1 wherein the haloalkanoate is a compound corresponding to the formula $X(CH_2)_nCOOZ$ in which X is chloro, bromo, or iodo; Z is an alkyl group containing 1-6 carbons; and n is an integer of 1-6.

8. The process of claim 7 wherein the haloalkanoate is ethyl chloroacetate.

9. The process of claim 7 wherein the haloalkanoate is methyl chloroacetate.

10. The process of claim 1 wherein the liquefied gas is a gas which has a critical temperature of at least 0° C.

11. The process of claim 10 wherein the liquefied gas has a critical temperature of at least 20° C.

12. The process of claim 11 wherein the liquefied gas is carbon dioxide.

13. The process of claim 1 wherein the quaternary ammonium ester is hydrolyzed with a base which is a Group IA or IIA metal hydroxide.

14. The process of claim 13 wherein the base is sodium hydroxide.

15. The process of claim 1 wherein the hydrolysis of the quaternary ammonium ester is also conducted in a liquefied gas as the solvent.

16. The process of claim 1 wherein the hydrolysis of the quaternary ammonium ester is conducted in a polar aprotic solvent in which the betaine is substantially insoluble.

* * * * *